United States Patent [19]

Pellegrino

[11] Patent Number: 5,358,140

[45] Date of Patent: Oct. 25, 1994

[54] ADHESIVE BANDAGE DISPENSING SYSTEM

[76] Inventor: Mark J. Pellegrino, 3426 Briton Cir. NW., Canton, Ohio 44708

[21] Appl. No.: 188,728

[22] Filed: Jan. 31, 1994

[51] Int. Cl.$^5$ .......................... G07F 11/66; B65H 3/58
[52] U.S. Cl. ........................................ 221/25; 221/26; 221/62; 221/70; 221/155; 221/197; 221/310; 206/440; 206/494
[58] Field of Search ............... 221/22, 25, 26, 28, 221/49, 62, 70, 155, 197, 309, 310, 312 R, 312 C; 206/440, 441, 820, 229, 233, 494

[56] References Cited

U.S. PATENT DOCUMENTS

| | | |
|---|---|---|
| 2,133,609 | 10/1938 | Eustis . |
| 3,217,954 | 11/1965 | Grant et al. . |
| 3,530,494 | 9/1970 | Baratta . |
| 3,835,992 | 9/1974 | Adams, IV . |
| 4,676,861 | 6/1987 | Bishop .............................. 221/70 X |
| 4,807,753 | 2/1989 | Goldstein ........................ 206/820 X |
| 4,993,586 | 2/1991 | Taulbee et al. . |
| 5,133,477 | 7/1992 | Etheredge, III et al. . |

FOREIGN PATENT DOCUMENTS 424342 5/1967 Switzerland ..................... 221/25 X

*Primary Examiner*—Robert P. Olszewski
*Assistant Examiner*—Dean A. Reichard
*Attorney, Agent, or Firm*—Michael Sand Co.

[57] ABSTRACT

An adhesive bandage dispensing system includes an elongated strand of individually sterile-wrapped adhesive bandages and a reusable dispenser for storing and dispensing the bandages. Each bandage is contained in a separate sterile compartment of an otherwise continuous wrapping material. Perforations formed in the wrapping material around each compartment allow the compartments to be individually opened. The strand is loaded into the dispenser, which is secured to a stable surface, so that the leading edge of the strand is frictionally held in biased guide flanges and protrudes from a dispensing opening defined by the flanges. The leading edge of the strand is pulled from the dispensing opening until an entire bandage is exposed, then the strand is pulled sharply to completely break the perforation, and the bandage can then be removed from the excess wrapping and prepared to be applied to a wound using both hands, if necessary. When the supply of bandages in the dispenser is exhausted, a refill bandage strand can be purchased in an inexpensive, waste-reducing package, and be used to replenish the supply of bandages in the reusable dispenser.

7 Claims, 6 Drawing Sheets

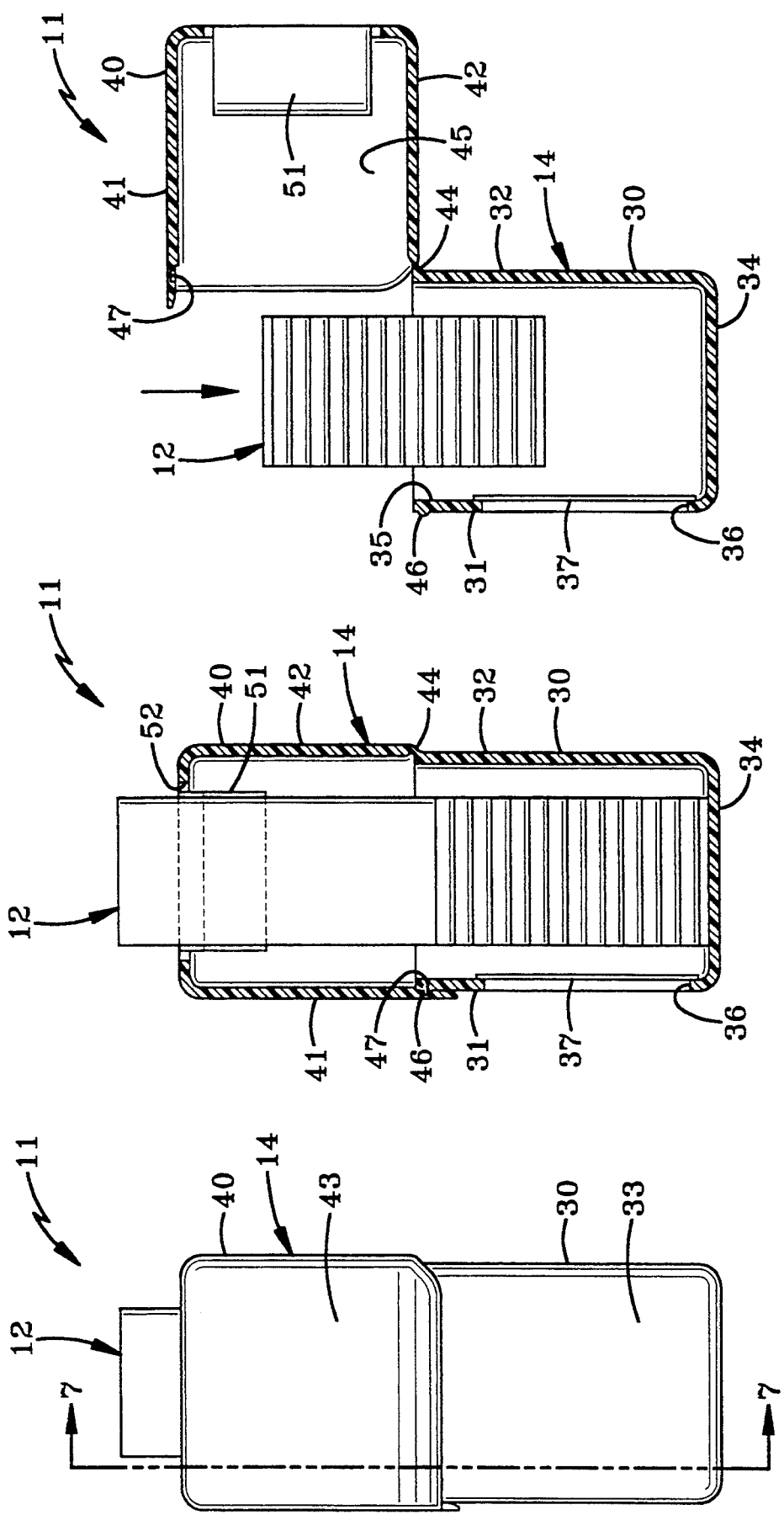

ADHESIVE BANDAGE DISPENSING SYSTEM

BACKGROUND OF THE INVENTION

1. Technical Field

The present invention relates to adhesive bandages and in particular to a system for dispensing adhesive bandages. More particularly, the invention is directed to an elongated strand of individually sterile-wrapped adhesive bandages and a package for dispensing and facilitating easy opening of the wrapped bandages.

2. Background Information

Heretofore, the handling of common adhesive bandages by health professionals and others, who often have only one free hand to grasp, open, and apply the dressing, has been difficult or impossible. The handling of such bandages arguably can even be a frustrating chore for a person having both hands available. This problem is a direct result of the necessary sterile wrapping in which each adhesive bandage typically is separately contained. Most adhesive bandages are manually opened either by transversely tearing the end of the wrapping off to expose an end of the bandage, or through the use of a string incorporated in the sterile wrapping which, when sharply pulled, causes a longitudinal tear in the wrapping to expose the bandage. These described well-known methods for opening adhesive bandages have proven unsatisfactory because two hands typically are needed during nearly the entire process of dispensing, opening and preparing the bandage for application to a wound.

The present invention provides an improved system for handling adhesive bandages by eliminating the need for the use of two hands during nearly the entire process of dispensing, opening and preparing the bandage for application to a wound. The solution to the above-described problem is accomplished by arranging individually sterile-wrapped bandages in an elongated strand, wherein each sterile wrapping is transversely perforated. The individual wrapped bandages of the strand are folded upon one another in an accordion-like fashion and contained in a dispenser which is secured to a tabletop or other stable surface. A guide opening formed in the dispenser frictionally holds the leading edge of the strand, so that the user of the bandages can easily dispense and open the sterile wrap of the bandage with one hand by applying a single sharp, pulling motion to the bandage causing the perforation to tear and exposing the bandage. Although a second hand may be briefly required to then apply the bandage to a wound, the present invention consistently saves time, effort and aggravation in the dispensing, opening and application of adhesive bandages, without sacrificing form, function, cost or the sterility of the bandages.

SUMMARY OF THE INVENTION

Objectives of the present invention include providing an adhesive bandage dispensing system, whereby the bandages can be quickly and easily dispensed, opened and applied to a wound using a single hand throughout most of the process.

Another objective of the present invention is to provide such an adhesive bandage dispensing system, whereby the bandages are sterile, familiar in form and effective in function, and whereby the dispensing system is cost-effective.

Still another objective of the present invention is to provide such an adhesive bandage dispensing system, whereby the dispenser is reusable and can be refilled with a fresh supply of bandages to further promote cost-effectiveness and reduce environmental waste resulting from discarded packaging.

These objectives and advantages are obtained by the adhesive bandage dispensing system of the present invention, the general nature of which may be stated as including a plurality of bandages, means for enveloping the bandages in an elongated strand and forming an individual sterile compartment for each of the bandages, wherein a generally continuous perforation is formed about each bandage in the envelope means, and dispensing means for containing the elongated strand of bandages, the dispensing means including means for guiding the elongated strand into a dispensing opening formed in the dispensing means, the guiding means providing resistance to the movement of a leading end of the strand out of the opening, so that upon the application of a force to the leading end of the strand adequate to overcome the resistance, the perforation completely breaks to expose at least a portion of a bandage for application of the bandage to a wound.

BRIEF DESCRIPTION OF THE DRAWINGS

The preferred embodiment of the invention, illustrative of the best mode in which applicant has contemplated applying the principles of the invention, is set forth in the following description and is shown in the drawings and is particularly and distinctly pointed out and set forth in the appended claims.

FIG. 4 is an end view of the dispensing system shown in FIGS. 1-3;

FIG. 5 is a transverse sectional view taken on line 5—5, FIG. 2, with hidden parts shown in broken lines, showing the strand of adhesive bandages contained in the dispenser;

FIG. 6 is a view similar to FIG. 5, showing the dispenser in an open position and the manner in which a strand of adhesive bandages is loaded into the opened dispenser;

Similar numerals refer to similar parts throughout the drawings.

DESCRIPTION OF THE PREFERRED EMBODIMENT

Figure 1:
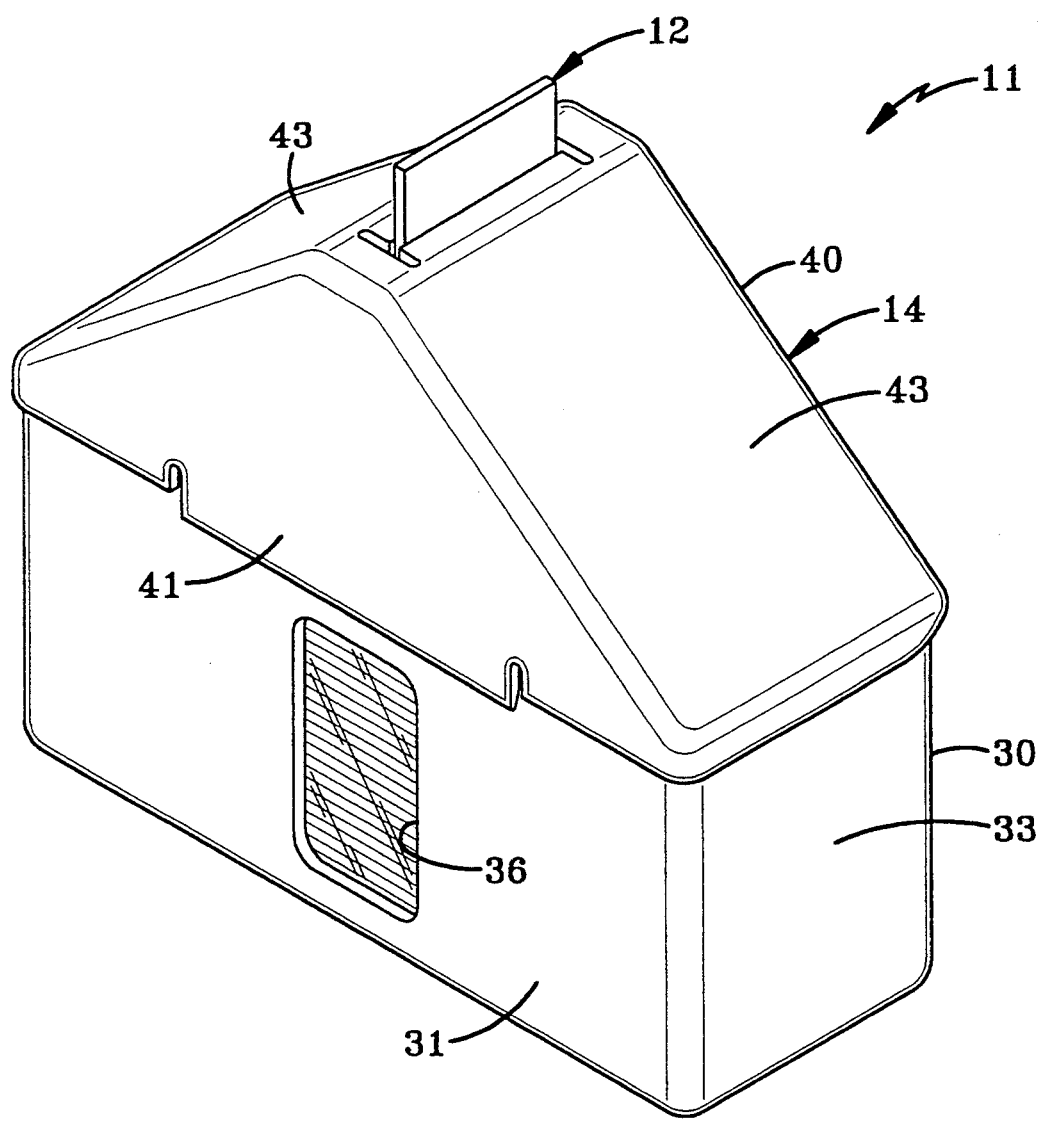
FIG. 1 is a perspective view of the adhesive bandage dispensing system of the present invention.
Figure 2:
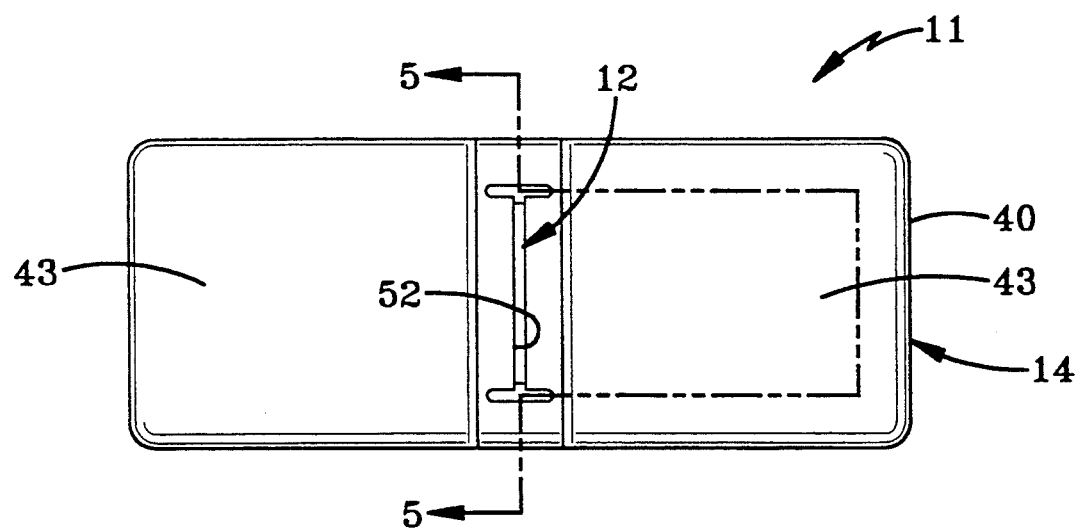
FIG. 2 is a top plan view of the dispensing system of FIG. 1.
Figure 3:
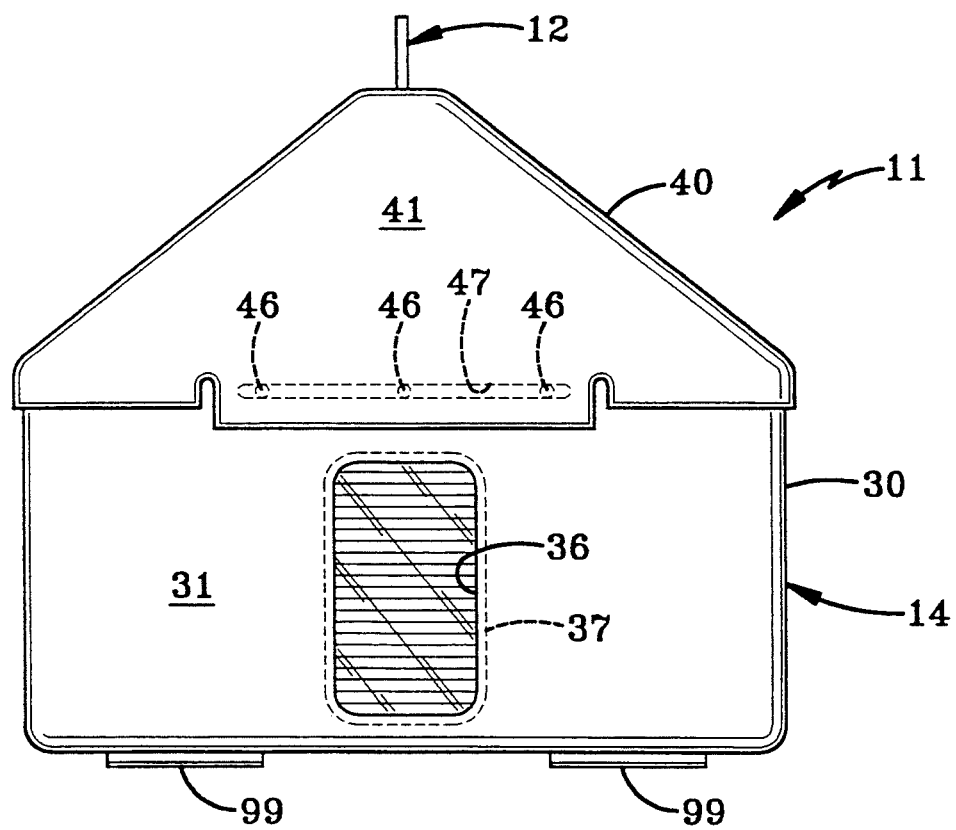
FIG. 3 is an elevational view of the dispensing system of FIGS. 1-2, with hidden parts shown in broken lines.

The improved adhesive bandage dispensing system of the present invention is indicated generally at 11 and is shown in FIG. 1. Bandage dispensing system 11 includes an elongated strand of individually sterile-wrapped adhesive bandages 12 and a dispenser 14.

Figure 8:
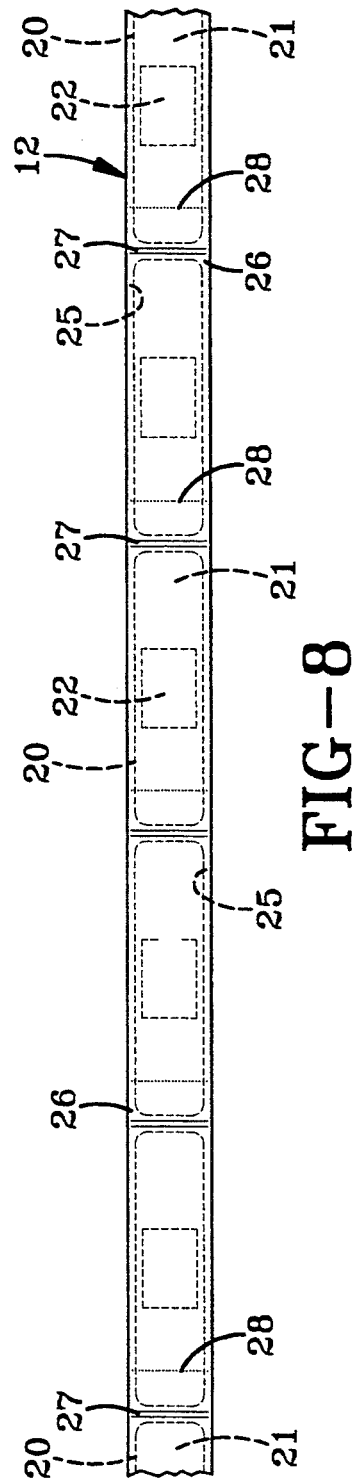
FIG. 8 is a reduced fragmentary top plan view of an elongated strand of individually sterile-wrapped adhesive bandages of the present invention, with hidden parts shown in broken lines.

Specifically, bandage strand 12 (FIG. 8) includes a plurality of individual adhesive bandages 20 of a type which are well known to the art and to the literature. Each adhesive bandage 20 typically includes a backing 21 formed of any suitable material such as plastic. One side of backing 21 is coated with a pressure sensitive adhesive (not shown), and further has a gauze dressing 22 disposed generally in the center of the adhesive-coated side of the backing. One or more pieces of release paper (not shown) are commonly used to protect adhesive-coated backing 21 of bandage 20 until the bandage is ready for use.

Gauze dressing 22 is intended to come in direct contact with a wound, and so it is important that the gauze dressing be kept sterile. To that end, each adhesive bandage 20 is contained in a separate sterile compartment 25 formed by wrapping material 26. Wrapping material 26 is of the familiar paper type currently used in the art. Specifically, wrapping material 26 is used to envelop bandages 20. A transverse seal 27 (FIGS. 7–8) is formed between each adjacent pair of transverse edges of bandages 20, to form sterile compartment 25 for each of the bandages. However, in accordance with one of the important features of the present invention, wrapping material 26 and adhesive bandages 20 contained therein form elongated bandage strand 12. Finally, and in accordance with another of the main features of the present invention, a continuous perforation 28 is formed in wrapping material 26 preferably intermediate gauze dressing 22 and the trailing edge of each bandage 20 (FIGS. 8–9), the function of which is explained in detail below.

Specifically, dispenser 14 preferably is formed of any suitable plastic and includes a lower portion 30 which is a generally rectangular-shaped box having front and rear walls 31 and 32, respectively, end walls 33, and a bottom wall 34 (FIGS. 1, 4, 5 and 7). The uppermost edges of front and rear walls 31, 32 and end walls 33 define an opening 35 (FIG. 6) into which bandage strand 12 is placed for dispensing, as will be described in greater detail below in the discussion of the operation of dispensing system 11. An opening 36 is formed in front wall 31 and enables a user of dispensing system 11 to immediately ascertain the approximate number of bandages 20 remaining in dispenser 14, without opening the dispenser. Opening 36 is covered with a transparent window 37 formed of any suitable material such as plastic for protecting bandage strand 12 from damage during shipping and use.

Figure 7:
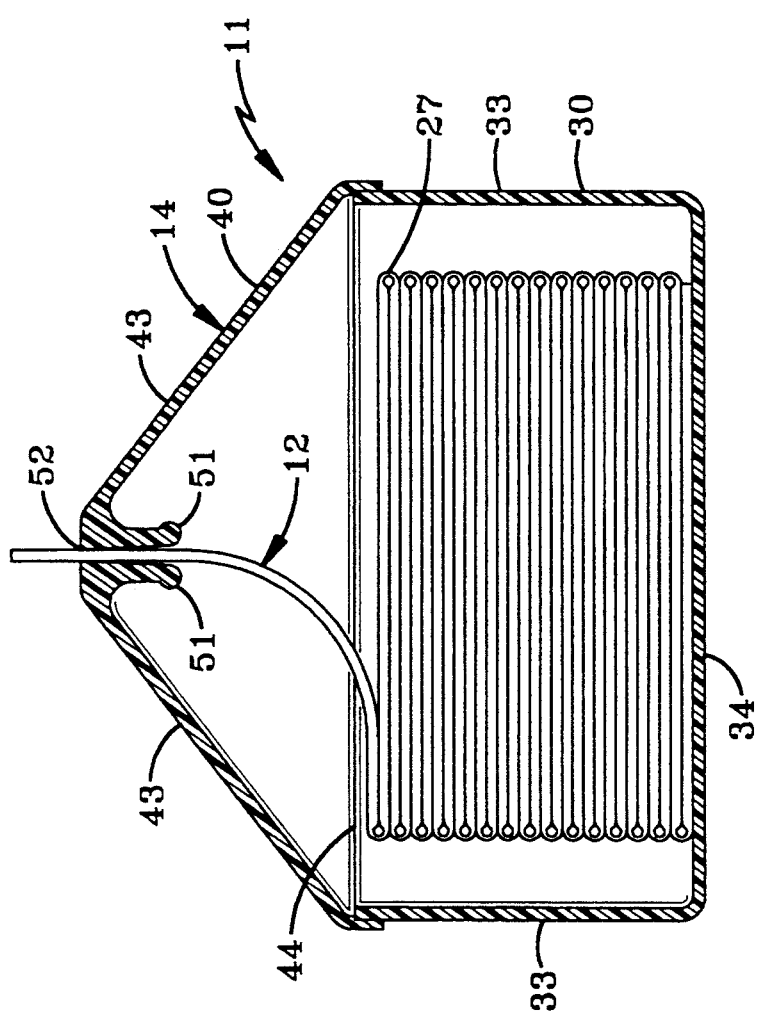
FIG. 7 is a longitudinal sectional view taken on line 7—7, FIG. 4.

Upper portion or hollow lid 40 of dispenser 14 is generally triangular-shaped and includes front and rear walls 41 and 42, respectively, and sloping top walls 43 (FIGS. 1–5). Upper portion 40 is formed integrally with lower portion 30 through a living hinge 44 which extends between and is formed integrally with the entire length of the uppermost and lowermost edges of rear walls 32 and 42 of the lower and upper portions, respectively, of dispenser 14 (FIGS. 5–7). An opening 45 defined by the lowermost edges of walls 41–43 of lid 40 is slightly larger than, but generally complementary in size to, opening 35 of lower portion 30. Thus, when lid 40 is moved from the opened to closed position, as best shown in FIGS. 6 and 5, respectively, the lid is securely latched in the closed position by the snapping engagement of a plurality of integrally formed nubs 46 (FIG. 3) of lower portion front wall 31 in recess 47 formed in lid front wall 41.

In accordance with still another of the primary features of the present invention, the uppermost edge of each of lid top walls 43 is formed with a depending guide flange 51 which is biased in the direction of its opposing guide flange, and which together define a dispensing opening 52 in dispenser lid 40 for bandages 20 (FIG. 7).

Bandage strand 12 is folded in an accordion-like fashion along transverse seals 27, as shown in FIG. 7, for placement in dispenser 14 in the manner shown in FIG. 6.

A double-sided pressure-sensitive adhesive tape or other suitable means 99 can be secured to bottom wall 34 of dispenser 14 for mounting the dispenser on a countertop or other stable surface, to ensure proper use and operation of dispensing system 11.

Figure 9:
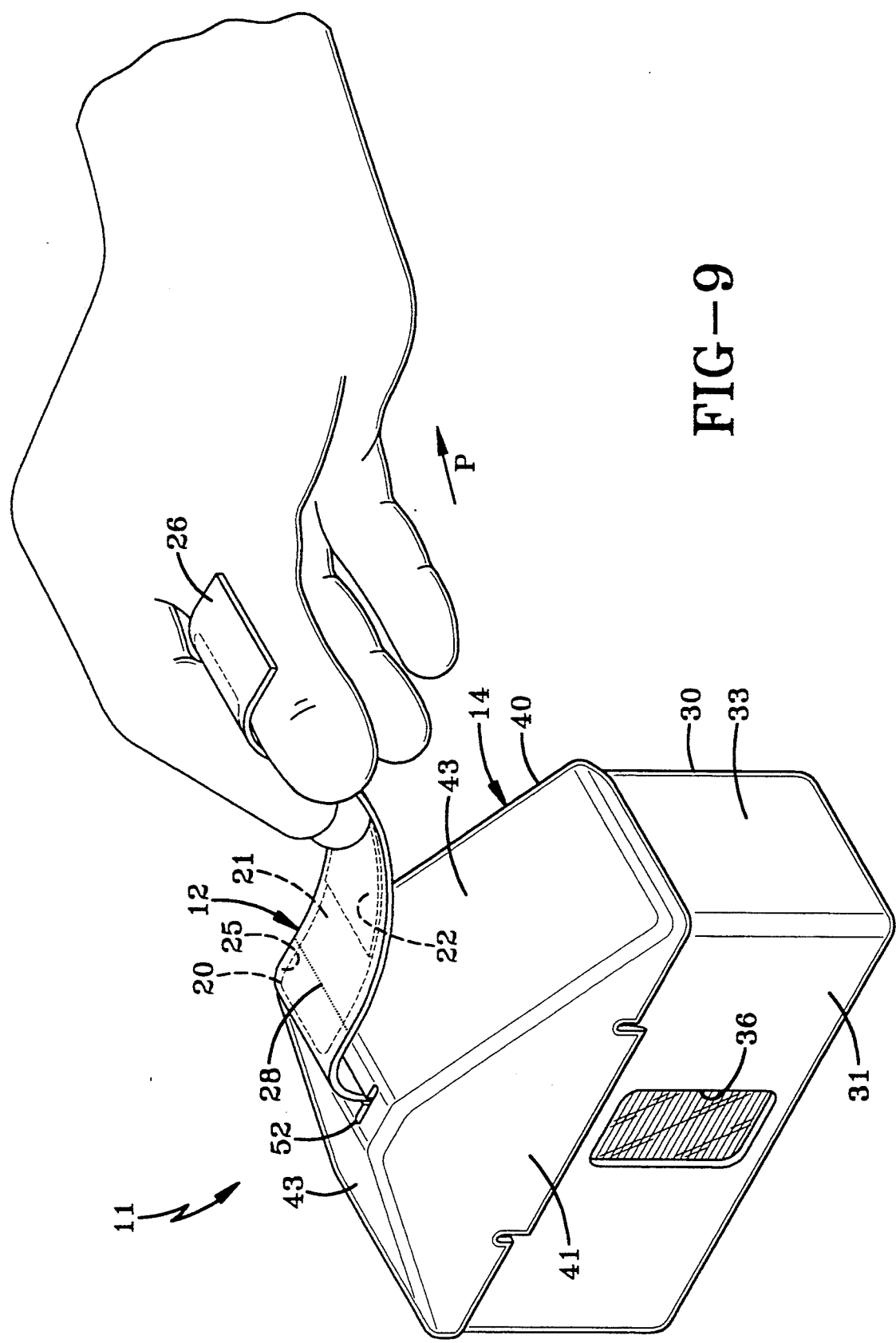
FIG. 9 is a fragmentary perspective view showing the manner in which an individual desiring to dispense, open and apply a bandage grasps and pulls the leading edge of the strand protruding from the dispenser.
Figure 10:
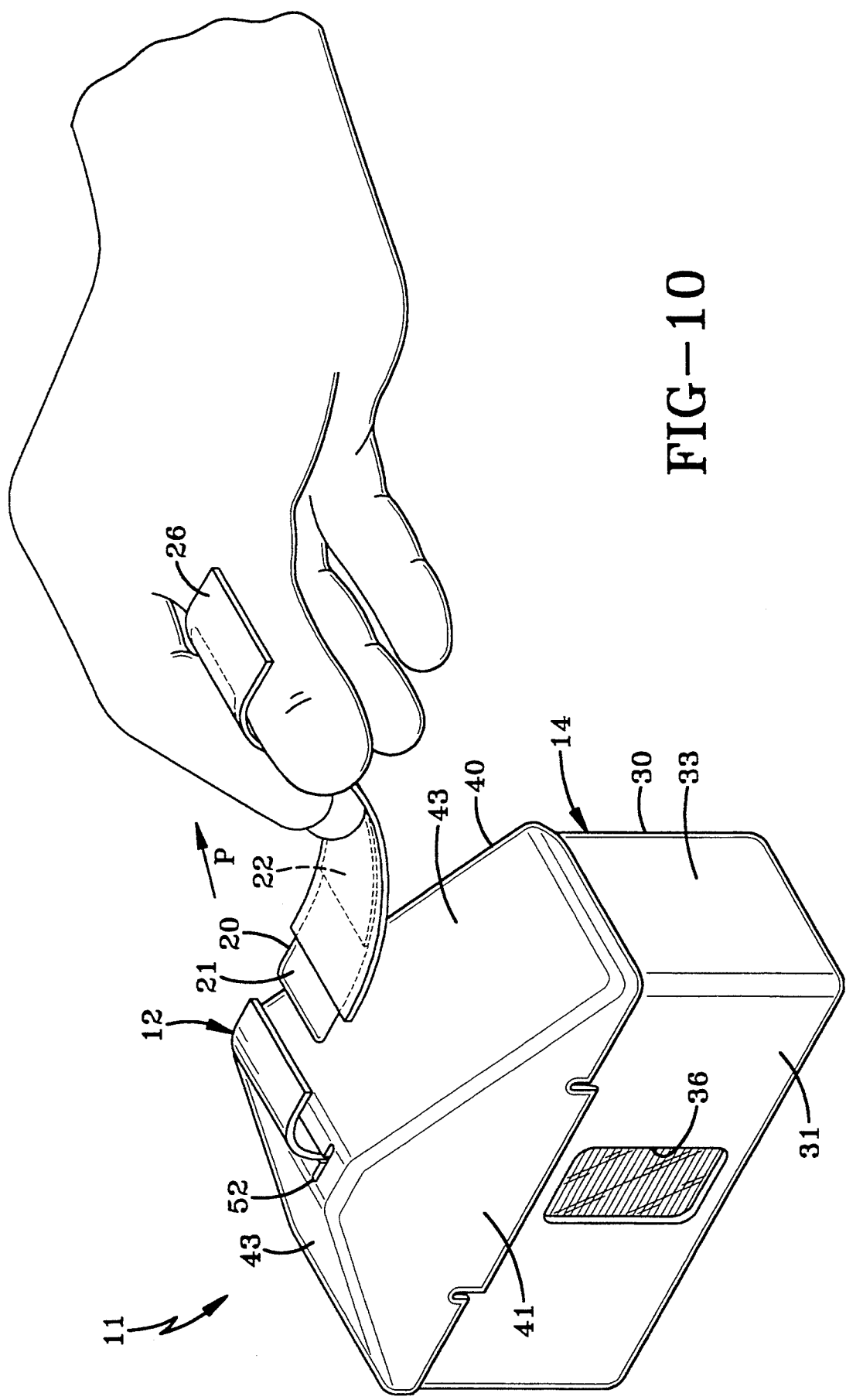
FIG. 10 is a continuation of the view of FIG. 9, showing the manner in which a bandage is exposed from its sterile wrapping by sharply pulling the strand to tear the perforation of the wrapping.

Dispensing system 11 is arranged and operated in the following manner. Dispensing system 11 is intended to be sold with the leading edge of the uppermost bandage 20 of strand 12 prefed into dispensing opening 52 as shown in FIGS. 1, 5 and 7. To ensure that the portion of bandage strand 12 protruding from dispenser 14 remains undamaged and usable, a small piece of common tape or other suitable means (not shown) can be used to removably fasten the protruding strand portion to one of dispenser top walls 43. An individual wishing to utilize a bandage 20 first secures dispenser 14 to a stable surface in the manner described hereinabove. The user grasps the leading edge of bandage strand 12 and pulls it out of dispensing opening 52 until an entire bandage is exposed as shown in FIG. 9, then snappingly pulls the strand in the general direction of arrow P as shown in FIG. 10, at which time wrapping perforation 28 completely breaks and the trailing edge of bandage 20 is exposed. It should be noted that the exact location of perforation 28 is not critical, so long as when the perforation is broken enough of bandage 20 is exposed to allow the user to readily grasp the bandage. The next bandage 20 then is positioned for use, with flanges 51 guiding strand 12 through dispensing opening 52 and frictionally holding the strand in the opening. It is also important to note that the present invention contemplates other suitable means for frictionally holding the strand in the opening, the use of which would not affect the overall concept of the invention.

It can be appreciated that the triangular shape of dispenser lid 40 is important to the proper functioning of dispensing system 11, inasmuch as a less severe slope of lid top walls 43 would fail to provide the necessary clearance to allow succeeding bandages 20 to move into position in dispensing opening 52 as the preceding bandages are dispensed. However, the slope of top walls 43 can be varied depending on the size and/or shape of bandages 20 to be dispensed, without affecting the concept of the invention.

Window 37 provides an easy means for visually checking the approximate amount of bandages left in dispenser 14, and the ability to open lid 40 provides for quick and easy refill of the dispenser as well as for quick and easy release of jams of strand 12 in dispensing opening 52 in the event that one should occur.

All of the above operations can be accomplished with one hand, after which both hands likely are needed for a brief moment to remove bandage 20 from the detached portion of wrapping material 26, and further to remove the release paper from the adhesive-coated backing 21. Bandage 20 then is ready to be applied to a wound.

It should be noted that preferably forming dispenser 14 from plastic is intended to encourage repeated reuse of the dispenser. This can be accomplished by selling refill bandage strands 12. Such a practice would save money for the consumer by eliminating the need to pay for more expensive packaging each time a purchase of adhesive bandages is made, and would also reduce environmental waste resulting from the discard of such packaging. However, dispenser 14 could be sold as a single use package formed of cardboard or another suitable material, without affecting the overall concept of the invention.

It should further be noted that the concept of the invention is intended to encompass dispensing systems of different sizes and shapes for different sizes and shapes of adhesive bandages, and could be extended to other dispensing applications, including dispensing applications for other types of dressings and the like where sterility and easy dispensing and opening are considerations.

Thus, it can be seen that the present invention provides an improved dispensing system for sterile adhesive bandages, which enables the bandages to be quickly and easily dispensed, opened and applied to a wound using a single hand throughout most of the process. This is accomplished in a system without changing the familiar form and function of adhesive bandages, and further without adversely affecting the sterility or cost of the bandages. Also, the dispenser can be refilled and reused thereby further reducing cost and environmental waste associated with single use packaging.

Accordingly, the improved adhesive bandage dispensing system is simplified, provides an effective, safe, inexpensive, and efficient system which achieves all the enumerated objectives, provides for eliminating difficulties encountered with prior adhesive bandage dispensing systems, and solves problems and obtains new results in the art.

In the foregoing description, certain terms have been used for brevity, clearness and understanding; but no unnecessary limitations are to be implied therefrom beyond the requirements of the prior art, because such terms are used for descriptive purposes and are intended to be broadly construed.

Moreover, the description and illustration of the invention is by way of example, and the scope of the invention is not limited to the exact details shown or described.

Having now described the features, discoveries and principles of the invention, the manner in which the improved adhesive bandage dispensing system is constructed, arranged and used, the characteristics of the construction and arrangement, and the advantageous, new and useful results obtained; the new and useful structures, devices, elements, arrangements, parts and combinations are set forth in the appended claims.

What is claimed is:

1. A dispensing system for sterile bandages, including:
   a) a plurality of bandages;
   b) means for enveloping said bandages in an elongated strand and forming an individual sterile compartment for each of the bandages, wherein a generally continuous perforation is formed about each bandage in said envelope means; and
   c) dispensing means for containing the elongated strand of bandages, said dispensing means including means for guiding said elongated strand into a dispensing opening formed in said dispensing means, said guiding means providing resistance to the movement of a leading end of said strand out of said opening, so that upon the application of a force to the leading end of the strand adequate to overcome said resistance, the perforation completely breaks to expose at least a portion of a bandage for application of the bandage to a wound.

2. The bandage dispensing system of claim 1, in which a transverse seal is formed in the envelope means between each adjacent pair of bandages.

3. The bandage dispensing system of claim 2, in which the elongated strand of bandages is folded in opposite alternating directions along the seals to form a stack of bandages for placement in the dispensing means.

4. The bandage dispensing system of claim 3, in which the dispensing means comprises a generally rectangular-shaped lower box portion and a generally triangular-shaped hollow lid portion; in which the dispensing opening is formed in said lid at its apex; in which the guiding means is a pair of spaced guide flanges which depend from said lid adjacent to and generally aligned with said opening and are each biased in the direction of the opposing guide flange; and in which means for securing said dispensing means to a stable surface is disposed on the lower box portion.

5. The bandage dispensing system of claim 4, in which the lid portion is formed integrally with the box portion through a living hinge; in which the lid portion is selectively opened and closed by a latching device formed in the lid portion and on the box portion; in which an opening is formed in the box portion for viewing the strand of bandages; in which the dispensing means is formed of plastic; and in which the securing means is a double-sided adhesive tape disposed on the bottom surface of said box portion.

6. The bandage dispensing system of claim 2, in which each bandage is an adhesive bandage having a backing coated with a pressure sensitive adhesive on one of the sides of said backing and a gauze dressing disposed generally in the center of the adhesive-coated side of said backing; and in which the generally continuous perforation is formed in the envelope means generally intermediate said gauze dressing and a trailing end of said bandage.

7. The bandage dispensing system of claim 6, in which said envelope means is formed of paper.

* * * * *